(12) United States Patent
Gomez et al.

(10) Patent No.: US 11,230,293 B2
(45) Date of Patent: Jan. 25, 2022

(54) METHOD FOR ROBUST VEHICLE OCCUPANCY DETECTION WITH VITAL SIGN MONITORING

(71) Applicant: IEE INTERNATIONAL ELECTRONICS & ENGINEERING S.A., Echternach (LU)

(72) Inventors: Oscar Gomez, Paris (FR); Muhammad-Zeeshan Khan, Kressbronn (DE); Jochen Landwehr, Trier (DE); Peter Larsen, Bereldange (LU); Dimitri Tatarinov, Trier (DE)

(73) Assignee: IEE INTERNATIONAL ELECTRONICS & ENGINEERING S.A., Echternach (LU)

( * ) Notice: Subject to any disclaimer, the term of this patent is extended or adjusted under 35 U.S.C. 154(b) by 0 days.

(21) Appl. No.: 16/973,362

(22) PCT Filed: Jun. 7, 2019

(86) PCT No.: PCT/EP2019/065007
§ 371 (c)(1),
(2) Date: Dec. 8, 2020

(87) PCT Pub. No.: WO2019/238575
PCT Pub. Date: Dec. 19, 2019

(65) Prior Publication Data
US 2021/0245763 A1    Aug. 12, 2021

(30) Foreign Application Priority Data

Jun. 11, 2018 (LU) .......................................... 100830
Aug. 3, 2018 (LU) .......................................... 100894

(51) Int. Cl.
*B60W 40/08* (2012.01)
*G01S 7/288* (2006.01)
(Continued)

(52) U.S. Cl.
CPC ........... *B60W 40/08* (2013.01); *G01S 7/2883* (2021.05); *G01S 7/292* (2013.01); *G01S 7/414* (2013.01);
(Continued)

(58) Field of Classification Search
CPC ................. B60W 50/14; B60W 40/08; B60W 2540/221; B60W 2040/0872;
(Continued)

(56) References Cited

U.S. PATENT DOCUMENTS 6,397,136 B1 * 5/2002 Breed ..................... G01S 15/04
180/273
6,753,780 B2    6/2004 Li
(Continued)

FOREIGN PATENT DOCUMENTS

| EP | 2472289 A1 | 7/2012 |
| WO | 2015022358 A1 | 2/2015 |
| WO | 2015140333 A1 | 9/2015 |

OTHER PUBLICATIONS

International Search Report corresponding to International Application No. PCT/EP2019/065007, dated Aug. 5, 2019, 4 pages.
(Continued)

*Primary Examiner* — Olumide Ajibade Akonai
(74) *Attorney, Agent, or Firm* — Reising Ethington P.C.

(57) ABSTRACT

A radar sensor system and a method for detecting an occupancy in an interior of a vehicle and with vital sign monitoring. The radar sensor system includes a radar transmitting unit, a radar receiving unit and a signal processing and control unit. The method includes: transmitting a radar wave towards a scene within the vehicle interior, receiving at least one radar wave that has been generated by reflection of the transmitted radar wave, decomposing the received radar wave into range, Doppler and angular information,
(Continued)

quantifying and tracking a movement in each region of interest by angular gating and range gating, detecting and monitoring vital signs of occupants in each region of interest, and determining whether quantified and tracked movements in the scene are related to an occupant or to external or internal disturbances, based on a fulfillment of at least one predefined condition concerning the and/or the detected vital signs.

15 Claims, 7 Drawing Sheets

(51) Int. Cl.
    *G01S 7/292* (2006.01)
    *G01S 7/41* (2006.01)
    *G01S 13/58* (2006.01)

(52) U.S. Cl.
    CPC ............ *G01S 7/415* (2013.01); *G01S 13/584* (2013.01); *B60W 2040/0881* (2013.01); *B60W 2420/52* (2013.01); *B60W 2420/60* (2013.01); *B60W 2540/221* (2020.02)

(58) Field of Classification Search
    CPC ..... B60W 2040/0881; B60W 2540/22; B60W 2540/043; B60W 2420/52; B60W 2420/60; G06F 3/017; G06K 9/00832; G06K 9/00369; B60R 16/037; B60R 21/01512; B60R 7/04; B60R 21/01534; B60R 21/01542; B60R 21/01554; B60R 21/0153; B60N 2/002; B60N 2002/0268; B60N 2002/0272; B60N 2002/981; G01S 13/56; G01S 13/88; G01S 7/414; G01S 13/584; G01S 7/415; G01S 7/2883; G01S 7/292; G01S 7/356; G01S 13/42; G01S 13/18; G01S 13/13; G01S 13/66; G01S 13/04; G01S 7/539; G01S 7/4802; A61B 5/18; A61B 5/1114; A61B 5/0507

See application file for complete search history.

(56) References Cited

U.S. PATENT DOCUMENTS

| | | | |
|---|---|---|---|
| 7,036,390 B2 | 5/2006 | Tsuchihashi et al. | |
| 7,570,785 B2 * | 8/2009 | Breed ................ | G06K 9/00228 382/100 |
| 7,887,089 B2 * | 2/2011 | Breed ............... | B60R 21/01538 280/735 |
| 8,152,198 B2 * | 4/2012 | Breed ................ | B60R 21/0152 280/735 |
| 10,214,118 B1 * | 2/2019 | Jain ...................... | B60N 2/0244 |
| 11,117,515 B2 * | 9/2021 | Ishibashi ................. | B60Q 9/00 |
| 2002/0029103 A1 | 3/2002 | Breed ................ | B60R 21/0154 701/45 |
| 2003/0201894 A1 * | 10/2003 | Li .......................... | B60N 2/002 340/573.1 |
| 2010/0225764 A1 | 9/2010 | Nizko | |
| 2012/0143786 A1 | 6/2012 | Karner | |
| 2015/0129343 A1 | 5/2015 | Teng et al. | |
| 2016/0200276 A1 | 7/2016 | Diewald | |
| 2017/0039835 A1 * | 2/2017 | Brankovic ............ | H01Q 9/285 |
| 2018/0170213 A1 | 6/2018 | Lu-Dac et al. | |
| 2018/0297489 A1 * | 10/2018 | Szawarski ................ | B60N 2/28 |
| 2019/0039549 A1 * | 2/2019 | O'Connor ......... | B60R 21/01512 |

OTHER PUBLICATIONS

Written Opinion corresponding to International Application No. PCT/EP2019/065007, dated Aug. 5, 2019, 6 pages.

* cited by examiner

METHOD FOR ROBUST VEHICLE OCCUPANCY DETECTION WITH VITAL SIGN MONITORING

TECHNICAL FIELD

The invention relates to a method of operating a radar sensor system for detecting an occupancy in an interior of a vehicle with vital sign monitoring, to a radar sensor system configured for automatically executing such method and a software module enabling automatically executing the method.

BACKGROUND

It is known in the art to use radar technology to detect objects of interest within an occupancy zone. For instance, US 2010/0225764 A1 describes a detection system and a method for such occupancy detection. The detection system can be applied to monitor vehicles or objects that could be used to transport unwanted materials into an area. The presence of objects of interest can include pedestrians, bicycles, automobile bumpers, glass surfaces, and vehicle wheel frames. The detection system comprises a plurality of sensors, which may be formed as frequency-modulated continuous-wave multi-beam radar sensors, including an entry sensor having a field of view oriented to detect object entry with respect to an entry portion of an occupancy volume, and an exit sensor having a field of view oriented to detect object exit with respect to an exit portion of the occupancy volume, the exit portion being different than the entry portion. The detection system further includes at least one approach sensor having a field of view oriented to detect object approach relative to the entry portion of the occupancy volume, and at least one retreat sensor having a field of view oriented to detect object retreat relative to the exit portion of the occupancy volume.

It is also known in the art to use radar technology for automotive seat occupant detection systems. Occupancy sensors based on radar technology offer advantages in comparison to other occupancy detection methods as their operation is contact-free and unnoticeable for vehicle occupants. Moreover, radar sensors can easily be integrated in the vehicle interior, for example behind plastic, plastic covers and diverse materials such as textiles, wood, stone, concrete, glass, and so forth.

Vehicle seat occupancy detection systems are nowadays widely used in vehicles, in particular in passenger cars, for instance for detection of left-behind pets and/or children, vital sign monitoring, vehicle seat occupancy detection for seat belt reminder (SBR) systems, or anti-theft alarm. Such vehicle seat occupancy detection systems can be employed for providing a seat occupancy signal for various appliances, for instance for the purpose of a seat belt reminder (SBR) system or an activation control for an auxiliary restraint system (ARS).

An output signal of a seat occupant detection and/or classification system is usually transferred to an electronic control unit of the vehicle to serve, for instance, as a means of assessing a potential activation of an installed vehicle passenger restraint system.

Further valuable information, usable as important input for Advanced Driver Assistance Systems (ADAS) could be provided by monitoring a vital sign of the detected person.

In U.S. Pat. No. 7,036,390 B2, a method for detecting a human body in a vehicle is described. A synthetic wave is obtained, which represents the synthesis (i.e. the superposition) of a transmitted wave radiated from a sensor and a reflected wave returned from a breathing human body, and the presence or absence of a human in the vehicle is detected from the envelope of the synthetic wave. The frequency of the transmitted wave is 4.7 GHz or higher. When the presence of a human is detected continuously for a predetermined length of time, it is determined that a human is present in the vehicle. When the interior of the vehicle reaches a temperature dangerous to a human, the sensor is activated. A device for monitoring temperature gradient inside the vehicle is provided, and the sensor is activated in advance when it is predicted by the device that the interior of the vehicle is likely to reach a dangerous temperature. When the rate of change of temperature inside the vehicle is mild, the sensor is operated at random timing for a predetermined length of time. When the interior of the vehicle reaches a dangerous temperature, and when the presence of a human is detected, an alarm is issued.

Furthermore, from U.S. Pat. No. 6,753,780 B2 a motion sensing system and method is known for detecting an occupant in a vehicle with enhanced sensitivity to detect small movement, such as movement caused by heartbeat and breathing of an occupant. The system includes a radar motion sensor located in a compartment of the vehicle. The radar sensor transmits and receives signals within the compartment and generates sensed signals. The system has a controller for converting the sensed signals to a frequency domain. The controller further processes the frequency domain of sensed signals and determines the presence of movement of an occupant due to one of heartbeat and breathing of the occupant. To this end, the controller compares the frequency domain of sensed signals within the frequency range to a predetermined frequency characteristic, and further identifies a frequency of the sensed signals indicative of movement of an occupant due to one of heartbeat and breathing.

WO 2015/140333 A1 describes a method for ascertaining whether an unattended child is present within an automotive vehicle. The method uses a radar sensor system comprising a transmitter, and at least one sensor and processing circuitry, and exploits a breathing motion detected by radar signals, for instance by applying autocorrelation and peak finding. The method comprises:

illuminating at least one occupiable position within the vehicle with radiation, the radiation exhibiting multiple frequencies;
 generating radar sensor signals from radiation reflected as a result of the transmitted radiation, a plurality of the radar sensor signals corresponding to different frequencies;
 operating the processing circuitry for generating, based on the radar sensor signals, a first indicator value, for instance R-value, the first indicator value indicating a degree of motion associated with the occupiable position;
 determining whether the first indicator value satisfies a first predetermined criterion;
 if the first indicator value satisfies the first predetermined criterion, generating, based on radar sensor signals, a second indicator value, the second indicator value indicating a degree of repetitive pattern within the radar sensor signals, for instance breathing pattern; and
 determining that an unattended child is present within the automotive vehicle if the second indicator value satisfies a second predetermined criterion.

The second indicator value may comprise a breathing signature representing the extent to which the sensor signals indicate that motion indicative of infant breathing child is detected.

Further, WO 2015/022358 A1 describes a method for sensing an occupancy status within an automotive vehicle using a radar sensor system. The radar sensor system comprises an antenna system, at least one sensor and a processing circuitry. The method comprises illuminating, using the antenna system, at least one occupiable position within the vehicle with continuous wave (CW signals), wherein the CW signals can be frequency modulated in time. At least one sensor signal reflected as a result of the CW signals is received using at least one sensor, wherein the at least one sensor is defining a plurality of receive channels (1, . . . i). Each receive channel has a different frequency ($f_1, \ldots, f_i$). Processing circuitry is operable for applying, for each receive channel (1, . . . , i), DC offset removal to the corresponding sensor signal to generate a modified signal; and generating, based on the modified signals, one or more occupancy status signals. In case of an employed FMCW radar sensor system, FFT processing is used to obtain the range of a detected occupant, and the vital signs of the occupant are obtained from the phase of the range FFT. The occupancy status signal indicate a property related to the at least one occupiable position. A system for carrying out the method is also disclosed. The techniques provide for in-vehicle occupant detection and classification (airbag suppression), for passenger presence detection and passenger's vital sign monitoring and for seat-belt reminder functionality (SBR). The radar system may consist of one or two (or four) outputs (I/Q) per channel. The received signal may be mixed down with a single channel demodulator or an I/Q demodulator into the baseband. An advanced signal processing including an auto calibration routine and clutter removal may be used to detect occupants and their vital sign (breathing and heart beat) and to determine their distance to the radar system.

In the article "*Non-Contact Estimation at 60 GHz for Human Vital Signs Monitoring Using a Robust Optimization Algorithm*" by Ting Zhang et al., Conference IEEE APS 2016, June 2016, Fajardo (Porto-Rico), United States, 2016, AP-S/URSI 2016. <hal-01340613>, an approach to estimate body movements related to vital activities by means of a 60 GHz Doppler radar is described, using robust optimization algorithms including signal autocorrelation analysis in order to extract heart-rate and breathing information from the radar signals.

It is therefore known in the art that a presence of a single vehicle passenger can be detected by conducting electromagnetic measurements such as Doppler radar techniques to measure, for instance, the passenger's breathing or heartbeat. Unfortunately, received radar waves are corrupted with noise if, for instance, a vehicle is moving over a rough surface, in the presence of strong wind gusts, in the presence of engine vibrations or in a carwash. This noise, which could be of high amplitude compared to the signal of a passenger that is desired to detect will inevitably lead to an increased number of false alarms, i.e. falls positives or false negatives.

SUMMARY

It is therefore an object of the invention to provide a method of robust vehicle occupancy detection with vital sign monitoring using radar technology, which is capable of reliably and robustly distinguishing between signals related to an occupant positioned in a specific region of interest in the vehicle interior and disturbing signals caused by vehicle interior events and/or events outside the vehicle, such as vehicle or sensor shaking induced by rough road, strong wind gusts, engine vibrations or car wash.

In one aspect of the present invention, the object may be achieved by a method of operating a radar sensor system for detecting an occupancy in an interior of a vehicle. The radar system comprises a radar transmitting unit that is configured for transmitting radar waves towards a scene within the vehicle interior, and a radar receiving unit that is configured for receiving radar waves that have been transmitted by the radar transmitting unit and have been reflected by an object within the scene.

Further, the radar sensor system includes a signal processing and control unit that is at least configured to derive range information, Doppler information and angle-of-arrival information from the received radar waves. Methods for deriving these types of information are well known to those skilled in the art and therefore need not to be described in more detail herein. Any method that appears suitable to those skilled in the art may be applied.

The phrases "configured to" and "configured for", as used in this application, shall in particular be understood as being specifically programmed, laid out, furnished or arranged. Further, in this application the terms "radar wave" and "radar signal" are used as synonyms, wherein the term "radar wave" may be used to more specifically describe an electromagnetic wave of a radar frequency traveling in free air, and the term "radar signal" shall be understood to relate either to an electromagnetic wave of a radar frequency that is carried by a transmission line or to a wire-bound signal that has been obtained by processing a received radar wave, for instance an IF (intermediate frequency) signal obtained by mixing a received radar wave with a local oscillator signal and/or demodulation.

The method includes at least the following steps, which are to be carried out in an iterative manner:
  operating the radar transmitting unit for transmitting a radar wave towards a scene within the vehicle interior,
  operating the radar receiving unit for receiving at least one radar wave that has been generated by reflection of the transmitted radar wave,
  operating the signal processing and control unit for:
    decomposing the received at least one radar wave into range, Doppler and angular information, and
    detecting and monitoring vital signs of occupants in each region of interest of a plurality of predefined different regions of interest.

According to an aspect of the invention, the step of operating the signal processing and control unit further includes:
  quantifying and tracking a movement in each region of interest of a plurality of predefined different regions of interest by angular gating and range gating, and
  for each region of interest, determining whether quantified and tracked movements in the scene are related to an occupant or to external or internal disturbances, based on a fulfillment of at least one predefined condition concerning the quantified and tracked movements and/or the detected and monitored vital signs, wherein the at least one predefined condition includes that if strong movement is present in all or several range regions of interest, a strong disturbance is likely to be present, and if movement is detected only in a region with a seating position, and vital signs are found, it is quite certain to assume that the seat is occupied.

The phrase "vital signs of an occupant", as used in this application, shall in particular be understood to encompass at least one out of heartbeat and breathing of the occupant. The term "occupant", as used in this application, shall in particular be understood to encompass human beings and pets.

It is a feature of at least some embodiments of the invention that by using a combination of range, Doppler and angle-of-arrival information, a robust vehicle occupancy detection method can be provided. The method enables to detect, quantify and track different movements in different regions of the scene. Internal and external motion can then be detected, separated and rejected or suppressed, for instance by range gating. The disclosed method is thus capable of reliably and robustly distinguishing between signals related to an occupant positioned in a specific region of interest in the vehicle interior and disturbance signals caused by vehicle interior events and/or events outside the vehicle.

Further, a presence of several occupants in the vehicle interior can be detected and their positions with respect to the radar sensor system be determined, and respective vital signs can be monitored simultaneously. Strong signals or disturbances that are present only outside a region of interest, e.g. a region including a seat row, do not affect any vital sign signals of occupants. As a consequence, a number of false alarms can be reduced and a robustness of the radar sensor system can be increased.

In preferred embodiments of the method, the step of determining whether quantified and tracked movements in the scene are related to an occupant or to external or internal disturbances is based on a temporal development of fulfillments of the at least one predefined condition concerning the quantified and tracked movements and the detected and monitored vital signs. In this way, a robustness of the method can be increased.

Preferably, the at least one predefined condition concerning the quantified and tracked movements and the detected and monitored vital signs includes consideration of a constraint regarding a number of passengers in the vehicle interior to be constant while the vehicle is driving. By use of this consideration, a plurality of potential occupancies in the interior of the vehicle can be ruled out, and a faster reactivity of the method can be achieved without compromising a sensitivity to false alarms.

Preferably, the step of decomposing the received radar waves into range, Doppler and angular information includes applying a fast Fourier transform to an intermediate frequency (IF) signal of the received radar waves for converting the IF signal of the received radar waves from the time domain into the range domain. In suitable embodiments, the range information can readily be obtained in this way.

In preferred embodiments of the method, the step of decomposing the received radar waves further includes removing a static scene from the fast Fourier transform of the IF signal of the received radar waves by making use of a fast Fourier transform of an IF signal of at least one previously received radar wave. By removing the static scene, movements in the balance of the fast Fourier transform of the IF signals of the received radar waves can be detected more easily.

The static scene may be removed by, without being limited to,
subtracting the fast Fourier transform of IF signals of the received radar waves computed in the previous iteration from the fast Fourier transform of IF signals of the currently received radar waves, or subtracting an average of a plurality of fast Fourier transforms of IF signals of received radar waves, computed at previous iterations, or by applying any other static scene removal method that appears to be suitable to those skilled in the art, such as applying a high pass filter or the like.

In preferred embodiments of the method, the step of quantifying and tracking a movement in each region of interest includes comparing an amount representing the quantified movement with at least one predefined detection threshold value for the quantity. This can allow for a fast and simple determination of a location of a maximum quantity within the gating.

Preferably, the at least one predefined detection threshold value for the quantity is a function of at least one out of vehicle speed and vehicle acceleration. In this way, the at least one predefined detection threshold value can be adjusted to match different driving situations and, by that, can reduce a number of false alarms. For instance, the at least one predefined detection threshold value may increase with increasing vehicle speed, at which larger disturbing signals by vehicle shaking induced by rough road driving are to be expected.

In preferred embodiments, determining a number of occupants in the vehicle interior can be supported by providing a signal from a wheel pressure sensor or sensors, or by providing analysis data from a wheel pressure sensor device. The wheel pressure information can be combined with information about the vehicle door activities for further support of determining the number of occupants.

In preferred embodiments of the method, the step of detecting and monitoring vital signs of occupants comprises calculating a phase signal from the fast Fourier transform of IF signals of the received radar waves at determined movements in each region of interest, and processing each phase signal by reconstructing the frequency domain signal into a phase-coherent time domain signal. In this way, the vital signs can readily be obtained from the received radar waves.

Preferably, the step of quantifying and tracking a movement in each region of interest includes calculating power integrals in predefined regions for each region of interest. In this way, a robust and reliable tracking of a movement in a specific region of interest can readily be accomplished.

In preferred embodiments of the method, the plurality of predefined different regions of interest includes at least one out of a range-azimuth, range-elevation or azimuth-elevation region of interest. In this way, a robustness of the method can be increased even more. In suitable embodiments of the radar sensor system, occupancy detection can be enabled for car interiors with larger cabin volume, which may, for instance, include several rows of seats. Further, detection of several occupants at different range-angle regions of interest can be enabled, and simultaneous monitoring of vital signs of these occupants can be accomplished.

Preferably, the method comprises a step of operating the signal processing and control unit for generating an output signal that is indicative of a determined occupancy of the vehicle interior. In this way, information concerning the determined occupancy of the vehicle interior can be transferred and assessed in a fast manner, and appropriate measures, such as warnings by an advanced driver assistance system (ADAS) can quickly be taken if applicable.

In another aspect of the invention, a radar sensor system for detecting an occupancy in an interior of the vehicle is provided. The radar sensor system comprises a radar transmitting unit that is configured for transmitting radar waves towards a scene within the vehicle interior, and a radar receiving unit that is configured for receiving radar waves that have been transmitted by the radar transmitting unit and have been reflected by an object within the scene.

Further, the radar sensor system includes a signal processing and control unit that is at least configured to derive range information, Doppler information and angle-of-arrival information from the received radar waves, to control operation of the radar transmitting unit and the radar receiving unit and to automatically execute steps of the method disclosed herein.

The benefits described in context with the disclosed method of operating a radar sensor system for detecting an occupancy in an interior of a vehicle apply to the radar sensor system to the full extent.

In preferred embodiments of the radar sensor system, the radar transmitting unit includes a plurality of radar transmitting antennas and the radar receiving unit includes a plurality of radar receiving antennas, and the radar transmitting antennas and the radar receiving antennas are configured to operate in a multiple-input and multiple-output (MIMO) configuration. In this way, an angular resolution of the radar sensor system can be improved. Finer angular resolution facilitates better distinguishing ability between signals related to an occupant positioned in a specific region of interest in the vehicle interior and disturbing signals caused by vehicle interior events and/or events outside the vehicle.

In one contemplated MIMO configuration with a plurality of transmitting antennas, each transmitting antenna is understood to be able to transmit radar waves in an independent manner that represent mutually orthogonal codes. Each receiving antenna is further understood to be able to receive radar waves that have been transmitted by any of the transmitting antennas and that have been reflected by an object without any cross talk disturbance.

Another contemplated MIMO configuration is the Time Division Multiplexing (TDM)-MIMO, which does not require orthogonal codes. Also, Binary Phase Modulated (BPM)-MIMO configurations are contemplated for use with this invention.

MIMO radar configurations provide benefits regarding enlarged size of virtual aperture, improved spatial resolution and less sensitivity to interference signals, as is well known in the art.

Preferably, the radar transmitting unit and the radar receiving unit form an integral unit and comprise a plurality of at least two transceiver antenna units, which are configured to work in a MIMO configuration. In this way, hardware parts can be saved and a more compact design of the radar sensor system can be achieved.

In preferred embodiments of the radar sensor system, the radar transmitting unit is configured to transmit frequency-modulated continuous radar waves. Frequency-modulated continuous wave (FMCVV) radar sensor systems are well known in the art to be able to provide received radar waves from which range information, Doppler information and angle-of-arrival information can be derived.

In yet another aspect of the invention, a software module is provided for controlling automatic execution of the method disclosed herein.

The method steps to be conducted are converted into a program code of the software module, wherein the program code is stored on a non-transitory computer-readable medium, such as a digital memory unit of the radar sensor system, and is executable by a processor unit of the radar sensor system. Preferably, the digital memory unit and/or processor unit may be a digital memory unit and/or a processing unit of the signal processing and control unit of the radar sensor system. The processor unit may, alternatively or supplementary, be another processor unit that is especially assigned to execute at least some of the method steps.

The software module can enable a robust and reliable execution of the method and can allow for a fast modification of method steps.

These and other aspects of the invention will be apparent from and elucidated with reference to the embodiments described hereinafter.

It shall be pointed out that the features and measures detailed individually in the preceding description can be combined with one another in any technically meaningful manner and show further embodiments of the invention. The description characterizes and specifies at least one embodiment of the invention in particular in connection with the figures.

BRIEF DESCRIPTION OF THE DRAWINGS

Further details and advantages of the present invention will be apparent from the following detailed description of non-limiting embodiments with reference to the attached drawing, wherein.

DESCRIPTION OF PREFERRED EMBODIMENTS

Figure 1:
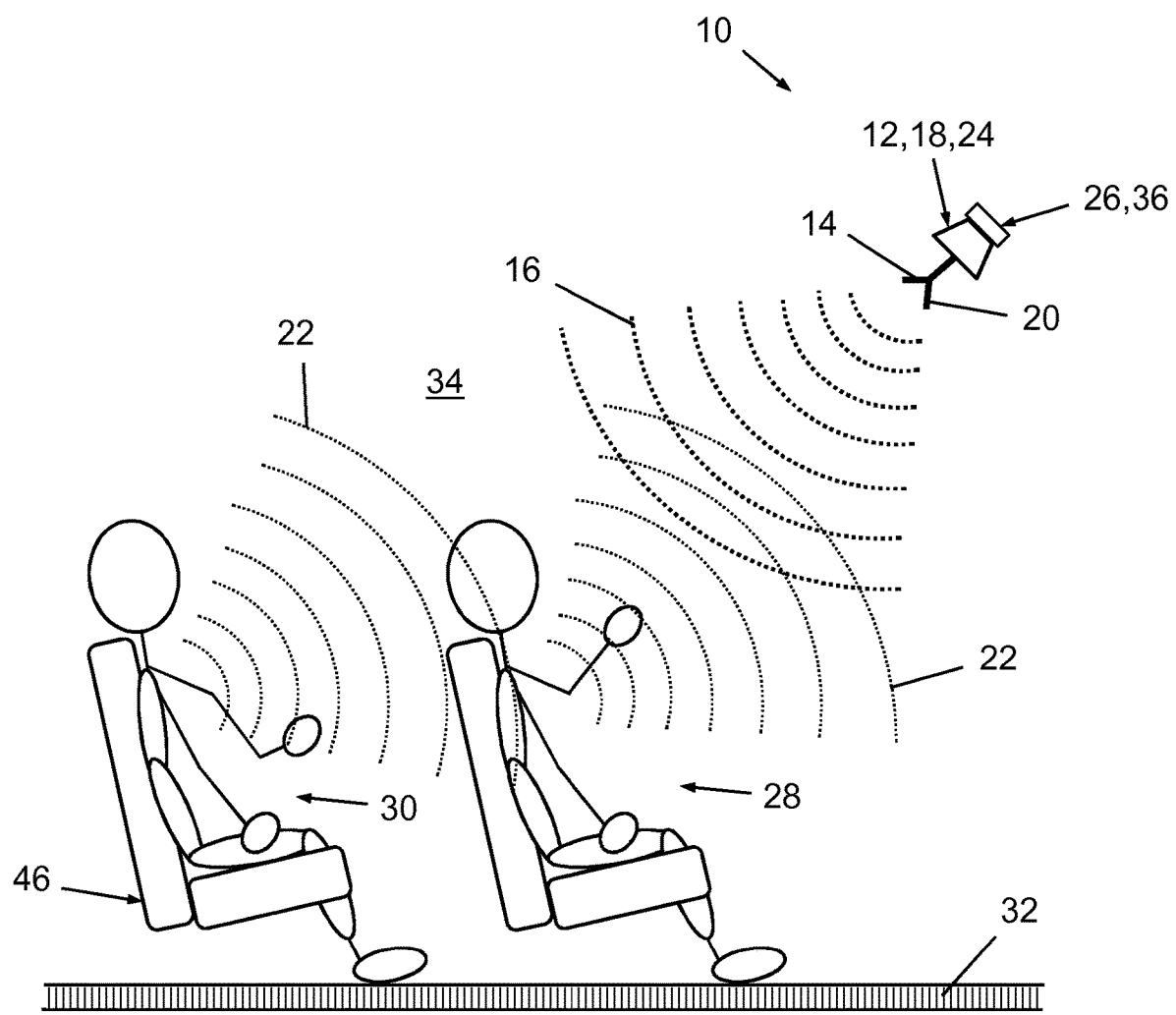
FIG. 1 schematically illustrates, in a side view, a configuration of an embodiment of a radar sensor system in accordance with the invention for detecting an occupancy in an interior of a vehicle and vital sign monitoring by executing an operating method in accordance with the invention.

FIG. 1 schematically illustrates, in a side view, a configuration of an embodiment of a radar sensor system 10 in accordance with the invention for detecting an occupancy in an interior 34 of a vehicle 32 with vital sign monitoring by executing an operating method in accordance with an embodiment of the invention. The interior 34 of the vehicle 32 is formed by a passenger car compartment of a sedan-type passenger car. FIG. 1 shows a side view of a passenger 28 occupying a driver's seat and another passenger 30 occupying one seat of three-seat rear bench 46 of the passenger car. More passengers (not shown) may be present, occupying a passenger front seat or other seats of the three-seat rear bench 46.

The radar sensor system 10 comprises a radar transmitting unit 12 that in this specific embodiment is configured to transmit frequency-modulated continuous radar waves (FMCW), and in this specific embodiment includes a plurality of three radar transmitting antennas 14. In other embodiments, the radar transmitting unit may be configured to transmit radar waves modulated by frequency-shift keying (FSK), or the radar transmitting unit may be configured to transmit radar pulses. Also, in other embodiments, the number of transmitting antennas may be different. In this specific embodiment, the radar transmitting unit 12 is configured for supplying the three radar transmitting antennas 14 with radar signals having a radar carrier frequency that is frequency-modulated with a saw-tooth pattern, as is known in the art, but other frequency modulation patterns such as triangular, sinusoidal modulation or any other pattern that appears suitable to those skilled in the art are also contemplated. In this specific embodiment, the radar carrier frequency of the radar sensor system 10 is selectable within a radar frequency range between 77 GHz and 81 GHz, but other frequency ranges, for instance a range between 57 GHz and 64 GHz, may be chosen, depending on the application. The radar transmitting antennas 14 are installed in a front region of the headliner and are directed rearwards. The radar transmitting unit 12 is configured for transmitting radar waves 16 via the radar transmitting antennas 14 towards a scene within the vehicle interior 34 given by the vehicle passenger compartment, and particularly towards a chest and an abdominal region of the driver 28 and other potentially present passengers 30.

The radar sensor system 10 further includes a radar receiving unit 18 having three radar receiving antennas 20 and being configured for receiving radar waves 22 that have been transmitted by the radar transmitting unit 12 and have been reflected by an object within the scene, among them the passengers 28, 30 that are present in the vehicle interior 34.

In this specific embodiment, each of the three radar transmitting antennas 14 is paired with one of the three radar receiving antennas 20 to be co-located in a monostatic arrangement, which is indicated in FIG. 1 by use of a combined symbol. In other embodiments, a bi-static arrangement or any other arrangement of an equal or unequal number of radar transmitting antennas and radar receiving antennas may also be possible. In this specific embodiment, the radar transmitting unit 12 and the radar receiving unit 18 each form an integral part of a transceiver unit 24, sharing common electronic circuitry and a common housing. In other embodiments, the radar transmitting unit and the radar receiving unit may be designed as separate units.

In this specific embodiment, the three transceiver antennas formed by the three radar transmitting antennas 14 and the three radar receiving antennas 20 are configured to operate in a multiple-input and multiple-output (MIMO) configuration.

In the MIMO configuration, each transceiver antenna is understood to be able to transmit radar waves in an independent manner that represent mutually orthogonal codes. Each transceiver antenna is further understood to be able to receive radar waves that have been transmitted by itself and any of the other transceiver antenna units and that have been reflected by an object, without any cross talk disturbance. The MIMO radar configuration provide benefits regarding enlarged size of virtual aperture, improved spatial resolution and less sensitivity to interference signals, as is well known in the art.

Furthermore, the radar sensor system 10 comprises a signal processing and control unit 26 that is connected to the radar transmitting unit 12 for controlling operation of the radar transmitting unit 12. The signal processing and control unit 26 is also connected to the radar receiving unit 18 for receiving radar signals generated by the radar receiving unit 18 from the received radar waves 22.

The signal processing and control unit 26 is configured to derive range information, Doppler information and angle-of-arrival information from the IF signals of the received radar signals. The signal processing and control unit 26 comprises a processor unit and a digital data memory unit (not shown) to which the processor unit has data access.

Figure 2A:
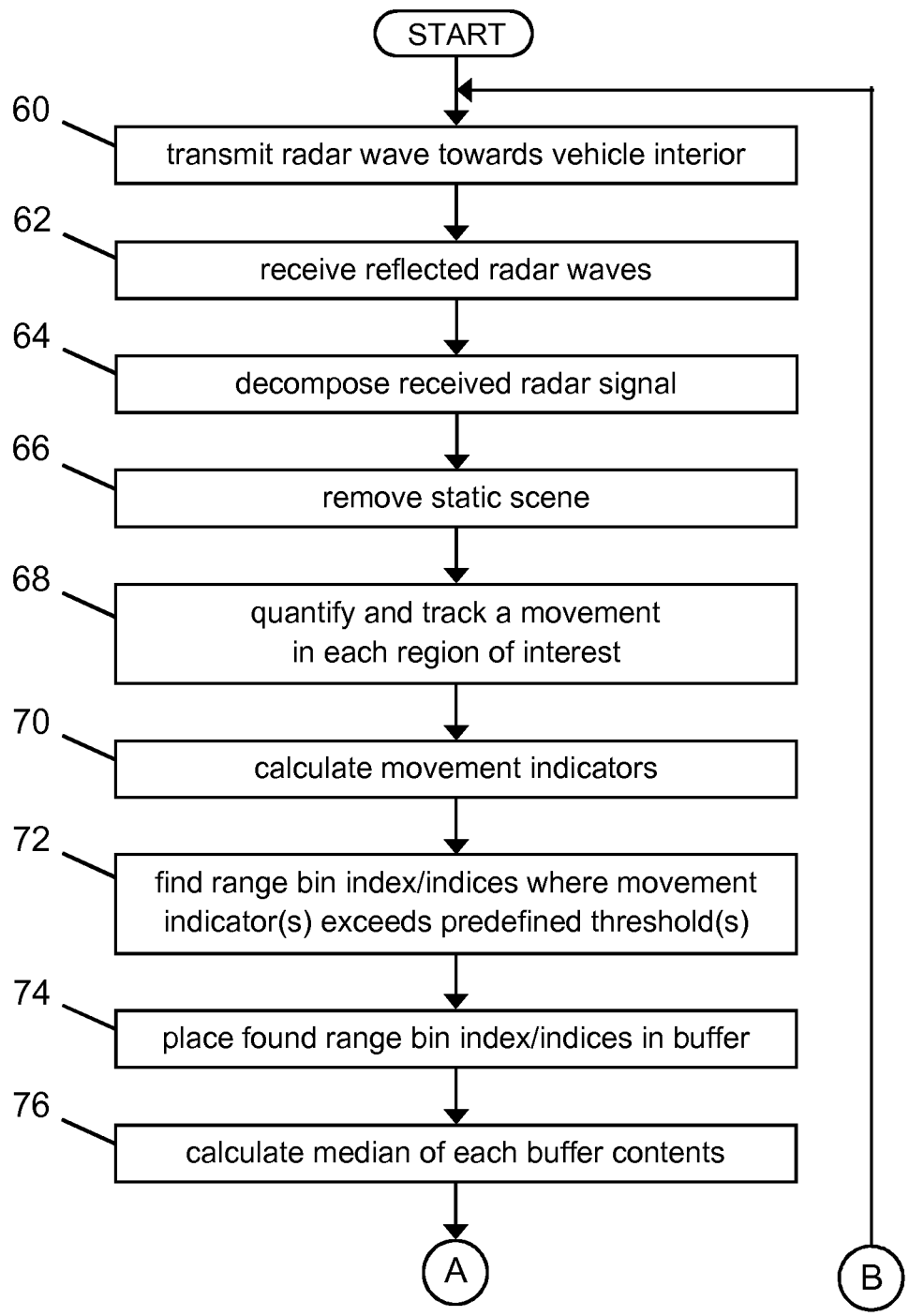
FIGS. 2a and 2b show a flowchart of an embodiment of the method in accordance with an embodiment of the invention of operating the radar sensor system pursuant to FIG. 1.
Figure 2B:
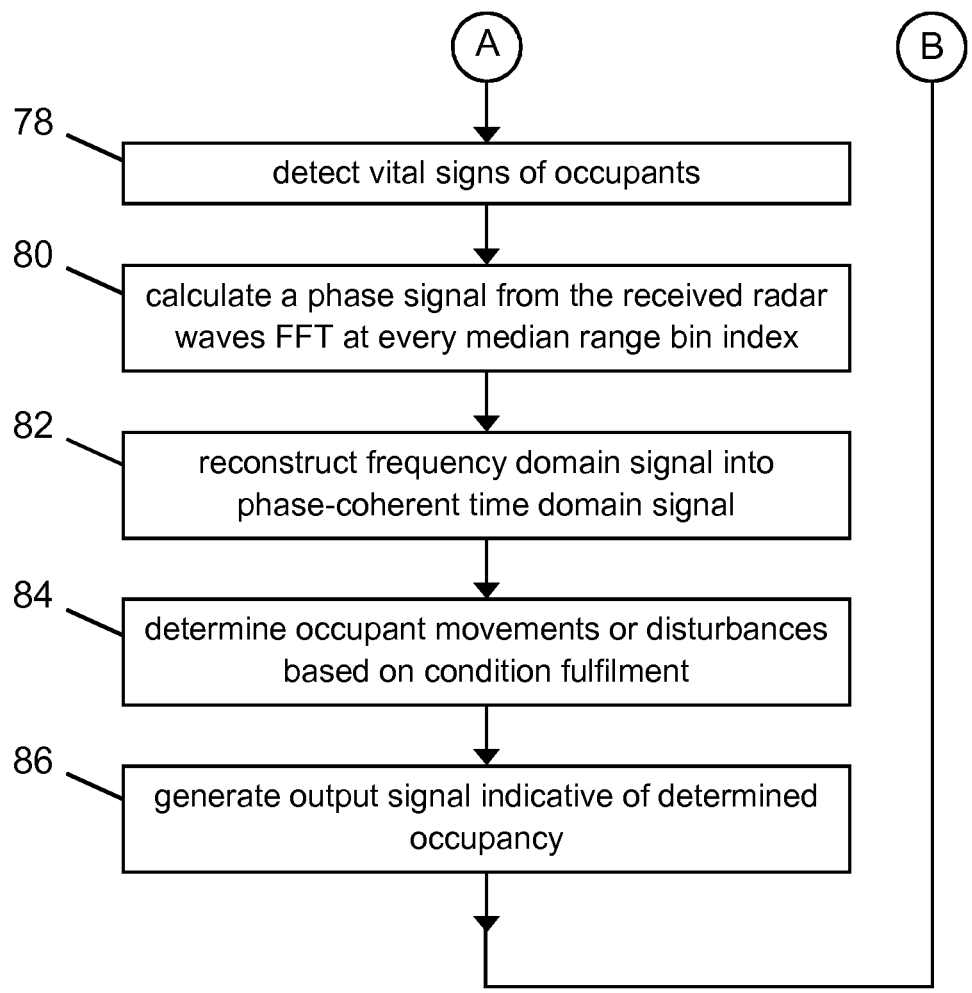

In the following, an embodiment of a method of operating the radar sensor system 10 for detecting an occupancy in the interior of the vehicle with vital sign monitoring will be described with reference to FIG. 1 and FIGS. 2a and 2b in general, which provides a flowchart of the method. In preparation of operating the radar sensor system 10, it shall be understood that all involved units and devices are in an operational state and configured as illustrated in FIG. 1.

In order to be able to carry out the method automatically and in a controlled way, the signal processing and control unit 26 comprises a software module 36. The method steps to be conducted are converted into a program code of the software module 36. The program code is implemented in the digital data memory unit of the signal processing and control unit 26 and is executable by the processor unit of the signal processing and control unit 26.

Execution of the method may be initiated for instance, but not limited to, by turning on the passenger car ignition. Other initiation methods are also possible. As shown in FIGS. 2a and 2b, the steps of the method are carried out in an iterative manner.

In a first step 60 of the method, the radar transmitting unit 12 is operated by the signal processing and control unit 26 for transmitting a radar wave 16 towards the vehicle passenger compartment. In another step 62, the radar receiving unit 18 is operated by the signal processing and control unit 26 for receiving radar waves 22 that have been transmitted by the radar transmitting unit 12 and that have been generated by reflection at any object in the scene, and in particular at the passengers 28, 30 that are present in the vehicle passenger compartment, and, more specifically, by reflection at the chest and the abdominal region of the passengers 28, 30.

In a next step 64, the signal processing and control unit 26 is operated to decompose an IF signal of the received radar signal into range information, Doppler information and angular information. To this end, the signal processing and control unit 26 applies a fast Fourier transform (FFT) to the IF signal of the received radar signal, which is a time domain signal, for extracting the range information. By that, the IF signal of the received radar signal is converted to the frequency domain. In another step 66, a static scene is removed by subtracting an FFT of an IF signal of a previously received radar signal, for example an IF signal of a radar signal that has been received in the previous iteration.

Figure 3:
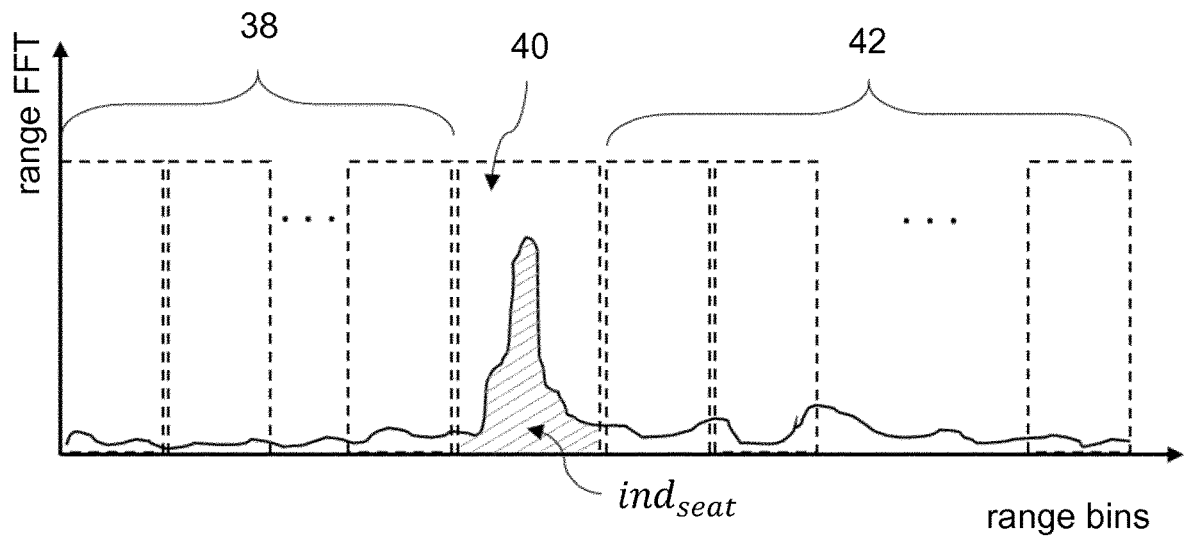
FIG. 3 shows a plot of range information after a step of decomposing received radar waves into range, Doppler and angular information.

FIG. 3 shows a plot of the range information after the step 64 of decomposing the IF signal of the received radar signal into range, Doppler and angular information and after the step 66 of removing the static scene. The range represented in FIG. 3 by range bins on the horizontal axis comprises a plurality of predefined regions of interest: a plurality of short-range regions of interest 38, a seat region of interest 40, which corresponds to a distance between the radar receiving unit 18 and the three-seat rear bench 46, and a plurality of long-range regions of interest 42. The range information of the FFT of the IF signal of the received radar signal shows a peak that is spread over a number of range bins in the seat region of interest 40.

In a next step 68 of the method, movement in each predefined region of interest 38, 40, 42 is quantified and tracked by angular gating and range gating.

To this end, a movement indicator $ind_{seat}$ is calculated that represents a quantity of the movement. In this specific embodiment, the movement indicator $ind_{seat}$ is given by a power integral to be calculated in predefined regions for each region of interest 38, 40, 42. Along the range information of the FFT of the IF signal of the received radar signal, maximum values are searched for by comparing the power integrals as amounts that represent the movement with a predefined detection threshold value for the power integral. If the amount exceeds the predefined detection threshold value, the range bin index of each one of the found maxima is placed into a buffer of predefined size. Then, the median of each buffer contents is calculated in every new iteration.

In this specific embodiment, the predefined detection threshold value for the power integral is a number that is constant for each predefined region of interest 38, 40, 42. In alternative embodiments, a predefined detection threshold value for the power integral may be a function of at least one out of vehicle speed and vehicle acceleration.

Figure 4:
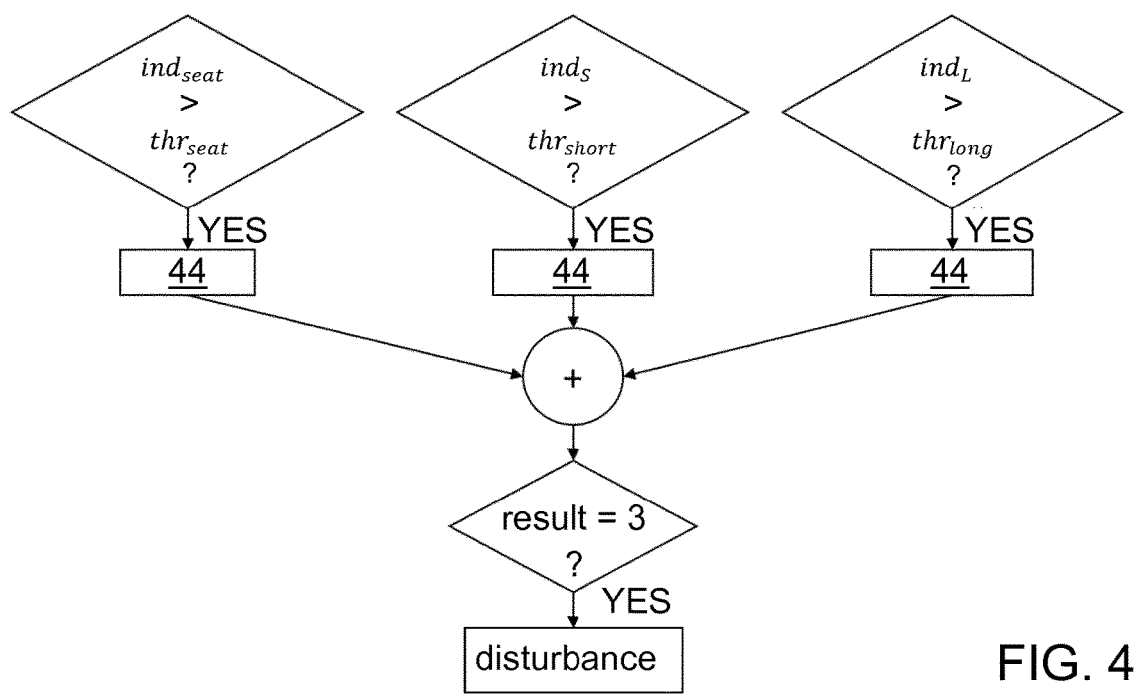
FIG. 4 is a detailed flowchart illustrating a step of quantifying and tracking a movement in regions of interest.

An example for detection of a disturbance is illustrated by FIG. 4, showing a detailed flowchart of the step 68 of quantifying and tracking a movement in three different regions of interest: a short-range region 38, the seat region 40 and a long-range region 42. For each region of interest 38, 40, 42 a detection threshold value $thr_{seat}$, $thr_{short}$, $thr_{long}$ for the power integral has been predefined. The various detection threshold values $thr_{seat}$, $thr_{short}$, $thr_{long}$ may be equal but do not have to be. In this specific embodiment, all three detection threshold values $thr_{seat}$, $thr_{short}$, $thr_{long}$ are mutually different.

Whenever a movement indicator $ind_{seat}$, $ind_s$, $ind_L$ exceeds the detection threshold value $thr_{seat}$, $thr_{short}$, $thr_{long}$ of the respective region of interest, a corresponding detection flag 44 is set to value "1", with the meaning that significant movement has been detected in the respective region of interest 38, 40, 42. If significant movement has been detected in all three regions of interest 38, 40, 42, it is quite certain to assume that a strong disturbance is present, which may be caused for instance by shaking the vehicle 32 by strong wind gusts, or the like.

Figure 5:
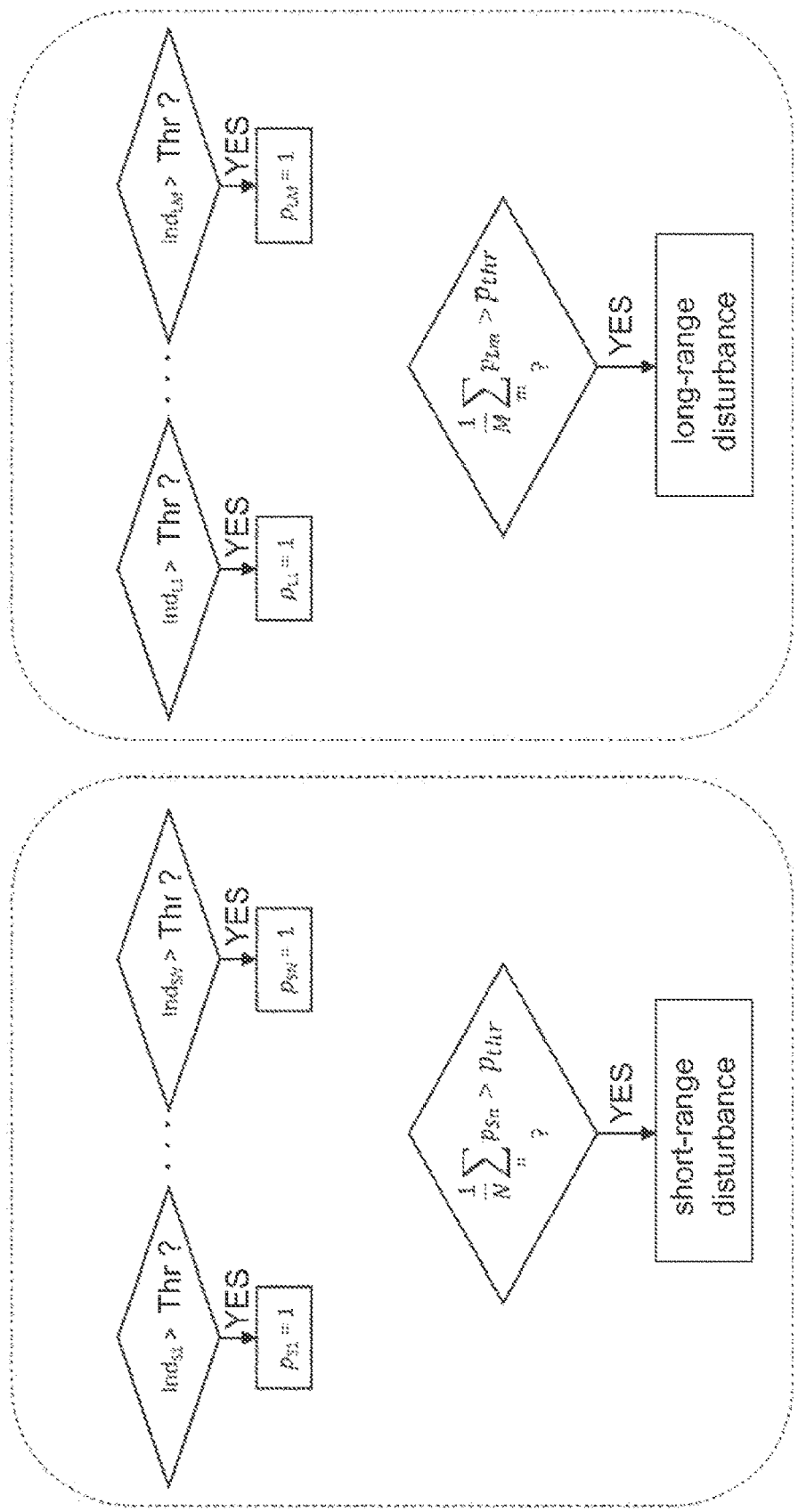
FIG. 5 is a detailed flowchart illustrating an alternative step of quantifying and tracking a movement in regions of interest, FIG. 6 schematically illustrates predefined different regions of interest covering a rear seat bench located in the vehicle passenger department pursuant to FIG. 1.

An alternative step of quantifying and tracking a movement in regions of interest is illustrated in the detailed flowchart of FIG. 5. Herein, the received radar signal FFT is divided in N short-range regions of interest, M long-range regions of interest and a seat region of interest.

The movement indicator $ind_{Si}$, $i=1, \ldots, N$ of each short-range region is compared against a corresponding detection threshold Thr, as shown in FIG. 5. Whenever the indicator of the $i^{th}$ short-range region exceeds the corresponding detection threshold, a detection flag $p_{si}$ is set to value "1", otherwise the variable detection flag $p_{si}$ remains at value "0". The values of $p_{si}$, $i=1, \ldots, N$ are then used to compute a probability, which is compared to a probability threshold $p_{thr}$ to determine if a short-range disturbance is present.

In a similar manner, movement indicators $ind_{Lj}$, $j=1, \ldots, M$ of each long-range region are compared against the corresponding detection threshold Thr, and long-range detection flags $p_{Lj}$, $j=1, \ldots, M$ are obtained. A probability is calculated from values of the long-range detection flags $p_{Lj}$, which is compared to a probability threshold $p_{thr}$ to determine if a long-range disturbance is present.

In a variation of this embodiment, variables $p_{si}$, $i=1, \ldots, N$ and $p_{Li}$, $j=1, M$ can take weighting values instead of "1" and "0".

Figure 6:
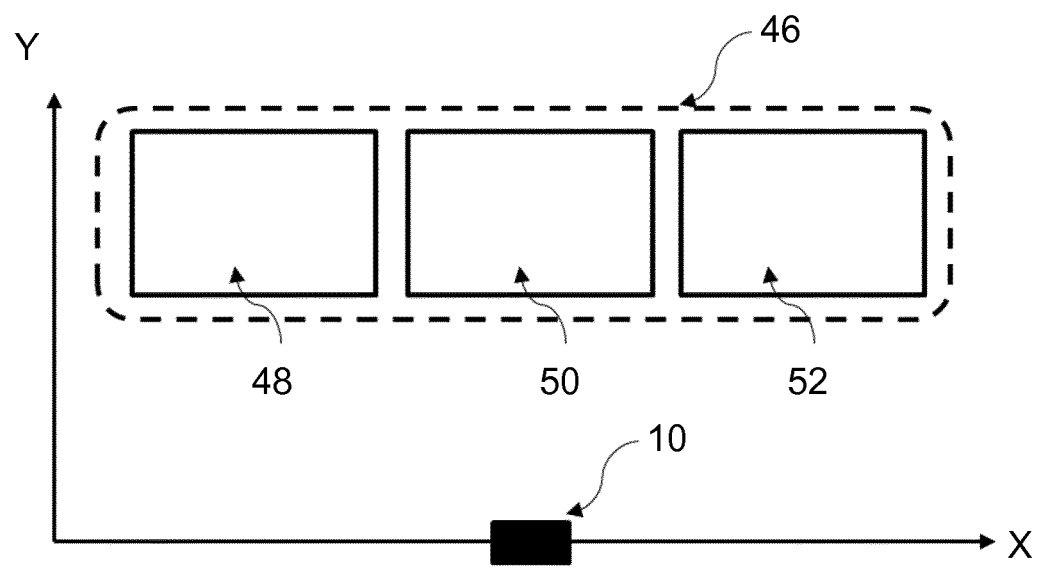

As described before, the three-seat rear bench 46 of the vehicle 32 lies in the range seat region 40 of interest pursuant to FIG. 3. A volume encompassing the three-seat rear bench 46 is further divided into three predefined regions of interest corresponding to a right seating position 48, a middle seating position 50 and a left seating position 52 (FIG. 6). The predefined regions of interest are defined in terms of range and azimuth (angular quantities), which can be converted to Cartesian coordinates x, y and z in the usual manner.

A movement indicator is calculated for each seating position 48, 50, 52 and compared to a detection threshold that corresponds to the respective seating position 48, 50, 52. To this end, a power integral is calculated in each predefined region, and a median of each buffer contents, which is the range bin index of each one of the found maxima, is calculated in every new iteration, as described before. Every new iteration of the method steps contributes to a temporal development of the buffers.

A buffer strategy regarding the temporal development of the buffer may be implemented similar to the one described in international application WO 2015/022358 A1.

As another step 78 of the method, vital signs of occupants, formed by a breathing movement, are detected and monitored in each region of interest 38, 40, 42. This is accomplished in a step 80 by calculating a phase signal from the FFT of the IF signal of the received radar waves 22 at determined movements in each region of interest 38, 40, 42, i.e. at every median of the buffer contents, and processing each phase signal in a step 82 of reconstructing the frequency domain signal into a phase-coherent time domain signal.

For each region of interest 38, 40, 42, it is determined in another step 84 whether quantified and tracked movements in the scene are related to an occupant or to external or internal disturbances, based on a fulfillment of predefined conditions concerning the quantified and tracked movements and/or detected and monitored vital signs.

In this specific embodiment, a first predefined condition is that if movement is detected in a seat region of interest 40 only, and vital signs are detected, it is determined that the movements in the scene are related to a seat occupant occupying the specific seat region of interest 40. A second predefined condition is that if movement is detected in a short-range region of interest 38, a seat region of interest 40 and a long-range region of interest 42, it is determined that the movements in the scene are not related to a seat occupant but are related to the presence of a strong disturbance such as the vehicle 32 shaking by wind gusts or by rough road driving.

In another step 86 of the method, the signal processing and control unit 26 is operated for generating an output signal that is indicative of the determined occupancy of the vehicle interior 34.

In a variation of the method, the step 84 of determining whether quantified and tracked movements in the scene are related to an occupant or to external or internal disturbances is based on a temporal development of fulfillments of the predefined conditions concerning the quantified and tracked movements and the detected and monitored vital signs. In this variation of the method, the fulfillment or non-fulfillment of the predefined conditions has to be persistent for a predefined number of iterations, which relates to a predefined qualification time.

The qualification time can either be decreased to improve reactivity at an expense of a higher susceptibility to false alarms, or can be increased to improve robustness at an expense of a reduced reactivity, i.e. a detection of an occupant, who is changing seat positions, might take a longer time.

In order to overcome the long qualification time issue, the predefined conditions concerning the quantified and tracked movements and the detected and monitored vital signs includes consideration of a constraint regarding a number of passengers in the vehicle interior 34 to be constant while the vehicle 32 is operated with closed vehicle doors (FIG. 1).

Figure 7:
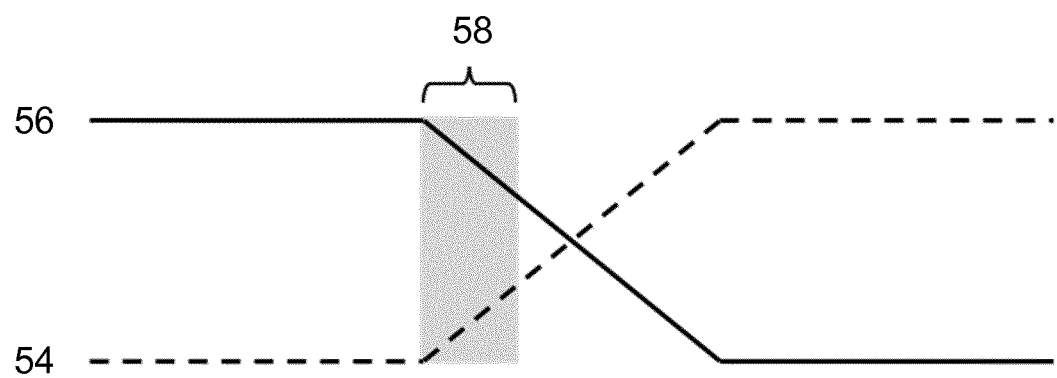
FIG. 7 illustrates a step of determining seat occupancy based on a temporal development of fulfillments of a predefined condition including consideration of a constraint regarding the number of passengers, and FIG. 8 schematically illustrates fast and slow transitions between determined occupancies.

FIG. 7 illustrates a step of determining seat occupancy based on a temporal development of fulfillments of a predefined condition including consideration of the above-mentioned constraint.

The occupancy states of the three-seat rear bench 46 can be represented by a 3-bit word, for instance (0,1,0), with the meaning: "Empty" (left seating position), "Occupied" (middle seating position), "Empty" (right seating position).

An occupant changing from one seating position to another is detected after a buffer value 54 that is related to a new seating position has been consecutively increased over a predefined time period 58 that is shorter than the qualification time, while another history buffer value 56 that is related to an old seating position has been consecutively decreased over the same time period 58. If this is detected, the occupancy state of the new seating position is set to "Occupied", while the occupancy state of the old seating position is immediately set to "Empty".

Figure 8:
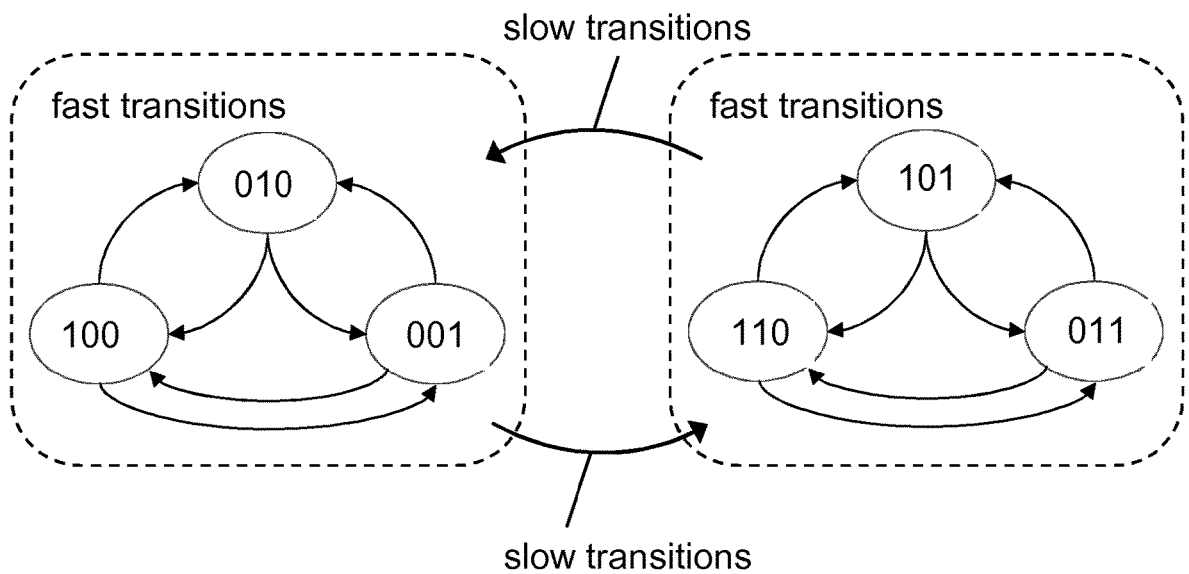

This occupancy state transition is carried out in any one of the cases of occupancy transitions with a constant number of occupants as shown in FIG. 8. These potential occupancy transitions, which can be called "fast transitions", as they do not require any opening and closing of doors of the vehicle 32, are shown for the three-seat rear bench 46 of the vehicle 32 and one seat occupant on the left-hand side of FIG. 8. On the right-hand side of FIG. 8, potential "fast occupancy transitions" for the three-seat rear bench 46 of the vehicle 32 and two seat occupants are shown. Potential occupancy transitions with a non-constant number of occupants, called "slow transitions", require opening and closing of doors of the vehicle 32, and are therefore determined after the regular qualification time.

While an embodiment of the invention has been illustrated and described in detail in the drawings and foregoing description, such illustration and description are to be considered illustrative or exemplary and not restrictive; the invention is not limited to the disclosed embodiments.

Other variations to be disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality, which is meant to express a quantity of at least two. The mere fact that certain measures are recited in mutually different dependent claims does not indicate that a combination of these measures cannot be used to advantage. Any reference signs in the claims should not be construed as limiting scope.

The invention claimed is:

1. A method of operating a radar sensor system for detecting an occupancy in an interior of a vehicle, with vital sign monitoring; the radar sensor system comprising:
   a radar transmitting unit being configured for transmitting radar waves towards a scene within the vehicle interior,
   a radar receiving unit being configured for receiving radar waves that have been transmitted by the radar transmitting unit and have been reflected by an object within the scene, and
   a signal processing and control unit that is at least configured to derive range information, Doppler information and angle-of-arrival information from the received radar waves;
   and the method including at least the following steps, which are to be carried out in an iterative manner:
   operating the radar transmitting unit for transmitting a radar wave towards a scene within the vehicle interior,
   operating the radar receiving unit for receiving at least one radar wave that has been generated by reflection of the transmitted radar wave,
   operating the signal processing and control unit for:
      decomposing the received at least one radar wave into range, Doppler and angular information, and
      detecting and monitoring vital signs of occupants in each region of interest of a plurality of predefined different regions of interest,
   wherein the step of operating the signal processing and control unit includes:
      quantifying and tracking a movement in each region of interest of a plurality of predefined different regions of interest by angular gating and range gating, and
      for each region of interest, determining whether quantified and tracked movements in the scene are related to an occupant or to external or internal disturbances, based on a fulfillment of at least one predefined condition concerning the quantified and tracked movements and/or the detected and monitored vital signs, wherein the at least one predefined condition includes that if movement is present in all or several range regions of interest, a disturbance is likely to be present, and if movement is detected only in a region with a seating position, and vital signs are found, it is determined that the seat is occupied.

2. The method as claimed in claim 1, wherein the step of determining whether quantified and tracked movements in the scene are related to an occupant or to external or internal disturbances is based on a temporal development of fulfillments of the at least one predefined condition concerning the quantified and tracked movements and the detected and monitored vital signs.

3. The method as claimed in claim 1, wherein the at least one predefined condition concerning the quantified and tracked movements and the detected and monitored vital signs includes consideration of a constraint regarding a number of passengers in the vehicle interior to be constant while the vehicle is driving.

4. The method as claimed in claim 1, wherein the step of decomposing the received radar waves into range, Doppler and angular information includes applying a fast Fourier transform to an intermediate frequency signal of the received radar waves for converting the intermediate frequency signal of the received radar waves from the time domain into the range domain.

5. The method as claimed in claim 4, wherein the step of decomposing the received radar waves further includes removing a static scene from the fast Fourier transform of the intermediate frequency signal of the received radar waves by making use of a fast Fourier transform of an intermediate frequency signal of at least one previously received radar waves.

6. The method as claimed in claim 1, wherein the step of quantifying and tracking a movement in each region of interest includes comparing an amount representing the quantified movement with at least one predefined detection threshold value for the quantity.

7. The method as claimed in claim 6, wherein the at least one predefined detection threshold value for the quantity is a function of at least one out of vehicle speed and vehicle acceleration.

8. The method as claimed in claim 1, wherein the step of detecting and monitoring vital signs of occupants comprises calculating a phase signal from the fast Fourier transform of IF signals of the received radar waves at determined movements in each region of interest, and processing each phase signal by reconstructing the frequency domain signal into a phase-coherent time domain signal.

9. The method as claimed in claim 1, wherein the step of quantifying and tracking a movement in each region of interest includes calculating power integrals in predefined regions for each region of interest.

10. The method as claimed in claim 1, wherein the plurality of predefined different regions of interest includes at least one out of a range-azimuth, range-elevation or azimuth-elevation region of interest.

11. The method as claimed in claim 1, comprising a step of operating the signal processing and control unit for generating an output signal that is indicative of the determined occupancy of the vehicle interior.

12. A radar sensor system for detecting an occupancy in an interior of a vehicle and for vital sign monitoring, the radar sensor system comprising:
   a radar transmitting unit being configured for transmitting radar waves towards a scene within the vehicle interior,
   a radar receiving unit being configured for receiving radar waves that have been transmitted by the radar transmitting unit and have been reflected by an object within the scene, and
   a signal processing and control unit that is at least configured to derive range information, Doppler information and angle-of-arrival information from the received radar waves, to control operation of the radar transmitting unit and the radar receiving unit and to automatically execute steps of the method of claim 1.

13. The radar sensor system as claimed in claim 12, wherein the radar transmitting unit includes a plurality of radar transmitting antennas and the radar receiving unit includes a plurality of radar receiving antennas, and the radar transmitting antennas and the radar receiving antennas are configured to operate in a multiple-input and multiple-output configuration.

14. The radar sensor system as claimed in claim 12, wherein the radar transmitting unit is configured to transmit frequency-modulated continuous radar waves.

15. A non-transitory digital data memory unit on which is stored a software module for controlling automatic execution of the method as claimed in claim 1, wherein method steps to be conducted are converted into a program code of the software module, wherein the program code is executable by a processor unit of the radar sensor system or a separate control unit.

* * * * *